(12) United States Patent
Cogdill

(10) Patent No.: US 6,481,065 B2
(45) Date of Patent: Nov. 19, 2002

(54) JEWELRY CLOSURE

(76) Inventor: Jolita Cogdill, P.O. Box 970, Aledo, TX (US) 76008

( * ) Notice: Subject to any disclaimer, the term of this patent is extended or adjusted under 35 U.S.C. 154(b) by 0 days.

(21) Appl. No.: 09/784,581

(22) Filed: Feb. 15, 2001

(65) Prior Publication Data

US 2002/0108217 A1 Aug. 15, 2002

(51) Int. Cl.[7] .............................................. A44B 21/00
(52) U.S. Cl. ...................... 24/303; 24/265 EC; 24/575; 24/326; 292/251.5; 63/14.4; 63/1.11; 403/DIG. 1
(58) Field of Search ................................. 24/575, 69 R, 24/68 J, 69 J, 70 J, 71 J, 303, 265 BC, 265 WS, 265 EC, 584.1, 587.1, 587.11, 326, 327, 652, 656; 292/251.5; 63/1.11, 3.1, 12, 14.4; 403/353, 340, DIG. 1

(56) References Cited

U.S. PATENT DOCUMENTS

| | | | | |
|---|---|---|---|---|
| 4,186,465 A | * | 2/1980 | Manning | 24/115 M |
| 4,231,137 A | * | 11/1980 | Fujimoto | 24/303 |
| 4,646,497 A | * | 3/1987 | Hoenle | 403/334 |
| 4,968,172 A | * | 11/1990 | Flading et al. | 403/24 |
| 5,099,659 A | | 3/1992 | Carranza | 63/2 |
| 5,145,276 A | * | 9/1992 | Demange | 285/360 |
| 5,149,109 A | * | 9/1992 | Jelinek et al. | 277/631 |
| 5,432,986 A | | 7/1995 | Sexton | 24/303 |
| 5,572,887 A | | 11/1996 | Geswelli | 63/3 |
| 5,664,298 A | | 9/1997 | Nessar-Ivanovic | 24/303 |
| 5,678,282 A | * | 10/1997 | Stewart | 24/68 J |
| 5,806,346 A | | 9/1998 | Schlinger et al. | 63/40 |
| 6,109,818 A | * | 8/2000 | Engel | 403/317 |
| 6,292,985 B1 | * | 9/2001 | Grunberger | 24/303 |

FOREIGN PATENT DOCUMENTS

| | | | | |
|---|---|---|---|---|
| GB | 2210130 A | * | 6/1989 | 403/DIG. 1 |
| JP | 10-179219 | * | 7/1998 | |

* cited by examiner

Primary Examiner—Robert J. Sandy
Assistant Examiner—André L. Jackson
(74) Attorney, Agent, or Firm—Bracewell & Patterson, LLP

(57) ABSTRACT

A jewelry closure created when a first jewelry clasp and a second jewelry clasp are aligned such that the central plane of the first jewelry clasp and the central plane of the second jewelry clasp are angularly offset with respect to each other. The central planes are offset to a degree such that each jewelry clasp can be rotated in a manner that a hole in an eyelet from one engagement region fits over a post from a second engagement region and a magnet in one jewelry clasp can magnetically engage with a magnet in the second jewelry clasp.

5 Claims, 2 Drawing Sheets

JEWELRY CLOSURE

BACKGROUND OF THE INVENTION

1. Technical Field

This invention relates generally to connection devices for items of jewelry and, more specifically, to clasps used to connect the ends of chains or cables used in jewelry design to thereby form a closure for the jewelry item.

2. Description of the Related Art

Bracelets and necklaces are normally provided with a clasp to close a strand of jewelry into a secure loop. The closure must provide a secure connection between the two ends of the jewelry and yet be easily opened by finger manipulation. Also, the closure must be designed so that it does not detract from the design or overall appearance of the jewelry item. Thus, among the important features a merchantable jewelry clasp must have are (1) it must effectively create a relatively strong closure and not come unfastened while the jewelry is being worn, (2) it must be easy to manipulate between the open and closed positions and (3) the jewelry closure must be aesthetically pleasing and not detract from the overall appearance of the piece. Many styles of clasps and closures have been produced. However, many of the available designs have failed in at least one of the three areas listed above.

What is needed is a jewelry closure that is easily connectable and provides a secure closure that is easily released by fingertip pressure. The closure should be both functionally sound and aesthetically pleasing yet relatively inexpensive to manufacture.

BRIEF SUMMARY OF THE INVENTION

It is an object of the present invention to provide a jewelry clasp that is easily connectable with a mating clasp to provide a secure closure, the closure being easily released by fingertip pressure.

It is another object of the present invention to provide an improved jewelry clasp which is connectable with a mating clasp to provide a closure means without spring-loaded elements, which become inelastic, need repair, and break.

It is yet another object of the present invention to provide an improved jewelry clasp that creates a closure that is both functionally sound and aesthetically pleasing.

It is yet another object of the present invention is to provide a jewelry clasp that is relatively inexpensive to manufacture.

The above objects are achieved by creating a jewelry closure which includes a first jewelry clasp and a second jewelry clasp. The clasps are aligned such that a central plane of the first jewelry clasp and a central plane of the second jewelry clasp are angularly offset with respect to each other. The central planes are offset to a degree such that each jewelry clasp can be rotated in a manner to allow a hole in an eyelet from an engagement region on one clasp to fit over a post from a mating engagement region on the other clasp. A magnet provided in at least one clasp is arranged to magnetically engage the second jewelry clasp.

Most preferably, a magnet is provided within an engagement region of each of the clasps, whereby rotation of the clasps in a manner that allows the eyelet from the first engagement region of the first clasp to fit over the post of the second engagement region of the second clasp causes the magnets of each clasp to be aligned and become magnetically engaged.

A method is also shown for joining two mating clasps to form a jewelry closure. A pair of clasps is provided as previously described, each having a top surface and a bottom surface and a proximate end and a distal end. The proximate end of each clasp is provided with two distinct engagement regions, the first engagement region being provided with an eyelet having a hole aligned with a central axis, the eyelet having a top surface and a bottom surface, the second engagement region being formed as a protrusion having an upper surface and a lower surface. The second engagement region is formed to include a post depending from the lower surface thereof with a central axis parallel to the central axis of the hole in the first engagement region. A magnet is installed inside at least one clasp.

The clasps are connected to form a closure by canting a first selected clasp about an axis which is generally within a central plane of the second respective clasp, the axis curving toward an outer extent of the clasp and being generally perpendicular to a cental axis of the eyelet hole in the first engagement region and the post in the second engagement region. The clasps can then be moved together with the first respective clasp continuing to be canted, such that when the two clasps are aligned and the central plane of the second clasp is angularly offset with respect to a central plane of the first clasp, the clasps can be rotated in a manner that the eyelet from the first engagement region of the first clasp fits over the post of the second engagement region of the second clasp and the magnet in the selected clasp can magnetically engage the other respective clasp.

Additional objects, features and advantages will be apparent in the written description which follows.

BRIEF DESCRIPTION OF THE DRAWINGS

The novel features believed characteristic of the invention are set forth in the appended claims. The invention itself however, as well as a preferred mode of use, will best be understood by reference to the following detailed description of an illustrative embodiment when read in conjunction with the accompanying drawings, wherein:

DETAILED DESCRIPTION OF THE PREFERRED EMBODIMENT

Figure 1:
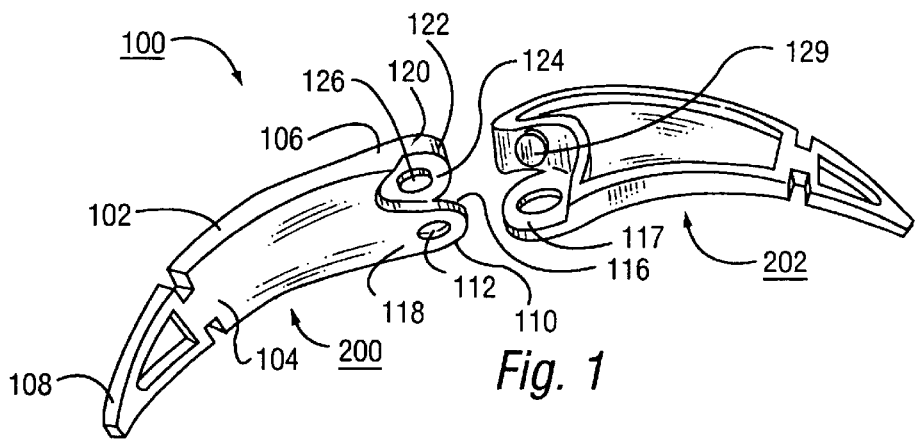
FIG. 1 is a perspective view of the jewelry closure of the invention showing the mating clasps used to form the closure.
Figure 3:
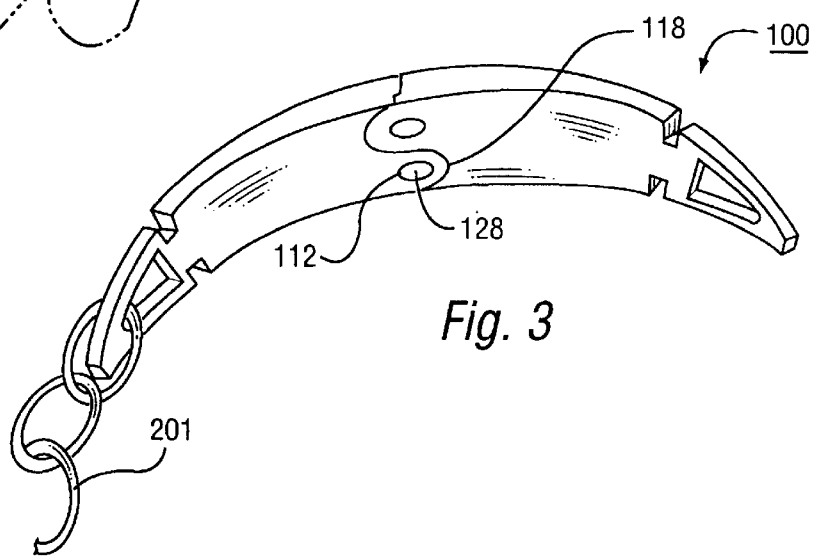
FIG. 3 is a bottom, perspective view of the joined jewelry clasps creating the jewelry closure of the invention.
Figure 4:
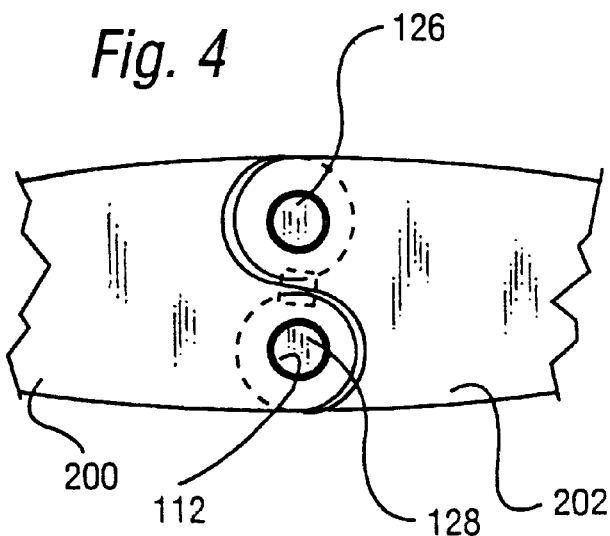
FIG. 4 is a partial, bottom view of the jewelry closure of the invention showing the engagement of the mating posts and eyelets of the mating clasps.

Referring first to FIG. 1 of the drawings, the preferred embodiment of a jewelry closure of the invention is illustrated generally as 100. Although the jewelry closure 100 is shown as the closure for a bracelet, it should be understood that the jewelry closure 100 may be used on any one of a wide variety of articles in need of a clasp or closure including: a necklace, purse, coat, etc.. Also, the closure 100 is made up of two mating clasps 200, 202, each of which is shown in isolated fashion in FIG. 1. As illustrated in FIG. 3, each clasp would normally have afixed thereto a chain or cable 201 which can assume any of a number of designs depending upon the tastes of the wearer.

Figure 2:
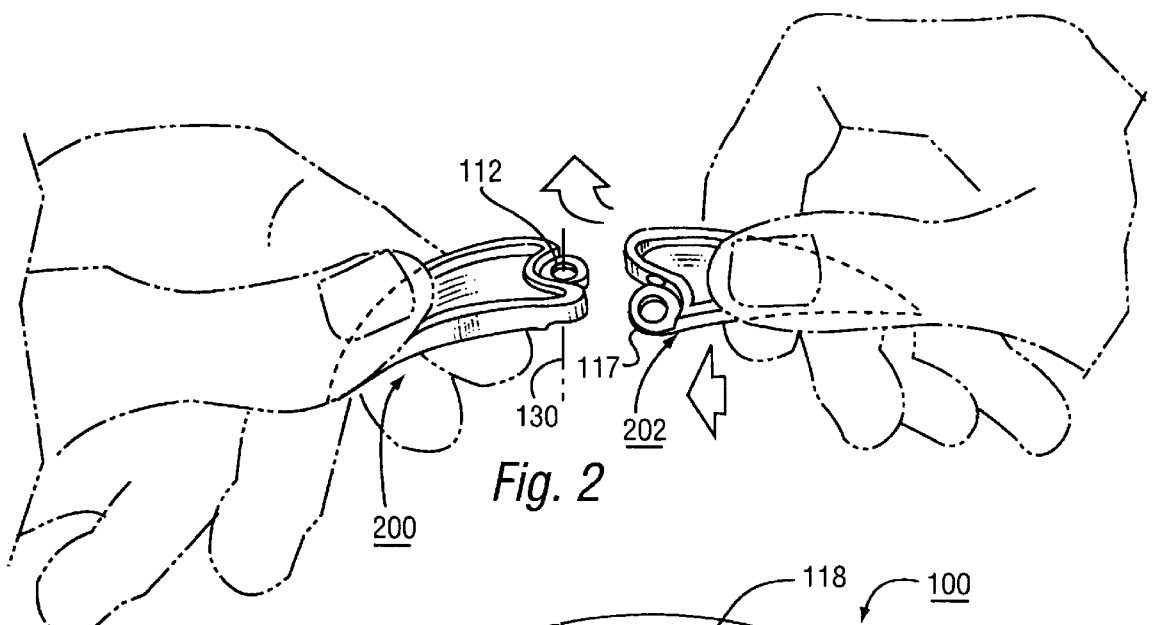
FIG. 2 is a simplified view of the fingers of a user's hands showing the movements needed to join the mating clasps and form the jewelry closure of the invention.

With reference to FIG. 1, the jewelry closure 100 includes a first clasp 200 having a top surface 102, a bottom surface 104, a proximate end 106, and a distal end 108. The proximate end 106 of the jewelry clasp 200 has a first engagement region 110 and a second engagement region 120. The first engagement region 110 has an eyelet 112 formed by a hole which transverses the engagement region from the top surface to the bottom surface thereof. The eyelet 112 has a central axis 130 (FIG. 2) and has a top surface 116 and a bottom surface 118.

Figure 5:
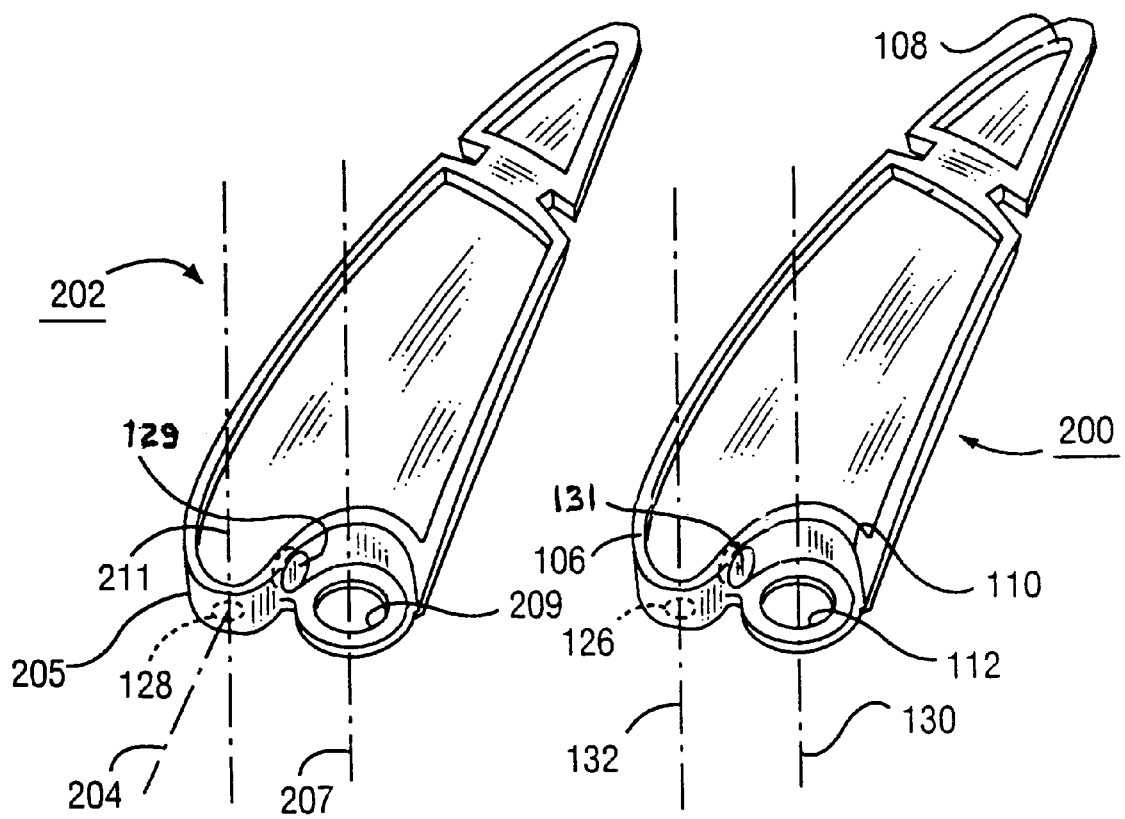
FIG. 5 is an isolated view of the two clasps which make up the jewelry closure showing the mating proximate ends of the clasps thereof.

The second engagement region 120 has an upper surface 122 and a lower surface 124. The lower surface 124 of the second engagement region 120 is in the same horizontal plane as the top surface 117 of the mating engagement region of the clasp 202. The lower surface 124 of the second engagement region 120 has a post 126 with a central axis 132 (FIG. 5) parallel to the central axis 130 of the eyelet 112 in the first engagement region 110. The post 126 has an outer extent 128 (FIG. 3) which is located in the same horizontal plane as the bottom surface 118 of eyelet 112 in first engagement region 110. A magnet 129 (FIGS. 1 and 5) is located in a mating engagement region of the second clasp 202 but may be located any place on the jewelry closure 100 that would serve to retain the post 126 of one jewelry clasp 200 within the eyelet (209 in FIG. 5) of a second jewelry clasp 202.

The first jewelry clasp 200 and the second jewelry clasp 202, each have a central plane (illustrated by the axis 204 in FIG. 5) that curves toward an outer extent 205. The central plane 204 is generally perpendicular to the cental axis 207 of the eyelet 209 and of the central axis 211 of the post provided in the second engagement region (shown in dotted lines in FIG. 5). A jewelry closure 100, shown in FIG. 3, is created when the first jewelry clasp 200 and the second jewelry clasp 202 are aligned such that the central plane 204 of the first jewelry clasp 200 and the central plane of the second jewelry clasp 202 are angularly offset or "canted" with respect to each other. This canted orientation allows the jewelry clasps 200, 202 to be rotated in a manner that the eyelet 112 from the first engagement region 110 of one clasp 200 fits over the mating post of the second engagement region of the second clasp 202. The permanent magnet 131 provided in the first jewelry clasp 200 can then magnetically engage the second jewelry clasp 202. The magnet 131 in the first jewelry clasp 200 may magnetically engage with another magnet in the second jewelry clasp 202 (such as magnet 129 in FIG. 5) or may magnetically engage with the second jewelry clasp itself if the second jewelry clasp 202 is made of a magnetically attractable material. an invention has veen descrived with several advantages. The jewelry clasps 200, 202 are easily connectable and provide a secure closure 100 that is easily released by fingertip pressure. The jewelry clasps 200,202 are provided with a closure means which does not require spring-loaded elements or other movable or stretchable elements, which become inelastic, need repair, and break. Because of the location and function of the mating eyelets and posts of the clasps, the jewelry closure 100 is aesthetically pleasing as well as functionally sound. Also, because the fist jewelry clasp 200 and the second jewelry clasp 202 are essentially mirror images of one another, they can be produced by relatively inexpensive manufacturing techniques.

The posts, eyelets and magnets create a unique closure mechanism. One mating clasp is canted relative to the other in order to allow the posts and eyelets on the respective clasps to engage in a rotating movement. The engagement of the eyelets and posts then prevents one from simply pulling one clasp apart from the other. The closure can only be opened by again canting one clasp relative to the other, simultaneously overcoming the magnetic attraction of the permanent magnets provided in the mating proximate ends of the clasps. This combination of magnetic attraction of the mating materials along with the required rotating movement of assembly provides a secure closure which is effective and yet simple in design.

While the invention is shown in only one of its forms, it is not thus limited but is susceptible to various changes and modifications without departing from the spirit thereof.

What is claimed is:

1. A jewelry closure, comprising:
   a pair of decorative clasps, each having a top surface and a bottom surface and a proximate end and a distal end;
   the proximate end having two distinct engagement regions with the first engagement region being an eyelet having a hole aligned with a central axis, the eyelet having a top surface and a bottom surface;
   the second engagement region being a protrusion having an upper surface and a lower surface;
   the second engagement region having a post depending from the lower surface thereof with a central axis parallel to the central axis of the hole in the first engagement region;
   a magnet located inside at least one clasp;
   the clasps being connectable by mating engagement of the respective posts and eyelets on the distinct engagement regions;
   the distal ends of each of the clasps being afixed to a flexible member which connects the clasps to form a closure;
   wherein at least one magnet is located in a selected engagement region of one of the clasps for magnetically securing the post of one clasp to the eyelet of the other clasp;
   wherein the post of a selected engagement region has an outer extent which is located in the same horizontal plane as the bottom surface of the first engagement region when the clasps are joined to form a closure;
   wherein the lower surface of the second engagement region is in the same horizontal plane as the top surface of the first engagement region when the clasps are joined to form a closure; and
   wherein a first clasp and a second clasp each have a central plane which curves toward an outer extent which is generally perpendicular to the cental axis of the eyelet hole in the first engagement region and the post in the second engagement region, such that when two clasps are aligned and the central planes are angularly offset with respect to each other, the clasps can be rotated in a manner that the eyelet from the first engagement region of the first clasp fits over the post of the second engagement region of the second clasp and the magnet in the selected clasp can magnetically engage the other respective clasp.

2. The closure of claim 1, wherein a magnet is located within an engagement region of each of the clasps whereby rotation of the clasps in the manner that the eyelet from the first engagement region of the first clasp fits over the post of the second engagement region of the second clasp causes the magnets of each clasp to be aligned and become magnetically engaged.

3. The closure of claim 2, wherein at least one of the clasps is made of a magnetically attractable material.

4. A method of joining two mating clasps to form a jewelry closure, the method comprising the steps of:

providing a pair of clasps, each having a top surface and a bottom surface and a proximate end and a distal end;

providing the proximate end of each clasp with two distinct engagement regions, the first engagement region being provided with an eyelet having a hole aligned with a central axis, the eyelet having a top surface and a bottom surface, the second engagement region being formed as a protrusion having an upper surface and a lower surface;

forming the second engagement region to include a post depending from the lower surface thereof with a central axis parallel to the central axis of the hole in the first engagement region;

installing a magnet inside at least one clasp; and connecting the clasps to form a closure by canting a first selected clasp about an axis which is generally within a central plane of the second respective clasp, the axis curving toward an outer extent of the clasp and being generally perpendicular to a cental axis of the eyelet hole in the first engagement region and the post in the second engagement region; and moving the clasps together with the first respective clasp continuing to be canted, such that when the two clasps are aligned and the central plane of the second clasp is angularly offset with respect to a central plane of the first clasp, the clasps can be rotated in a manner that the eyelet from the first engagement region of the first clasp fits over the post of the second engagement region of the second clasp and the magnet in the selected clasp can magnetically engage the other respective clasp.

5. The method of claim 4 wherein a magnet is provided within an engagement region of each of the clasps, whereby rotation of the clasps in the manner that the eyelet from the first engagement region of the first clasp fits over the post of the second engagement region of the second clasp causes the magnets of each clasp to be aligned and become magnetically engaged.

* * * * *